United States Patent
Primus et al.

(10) Patent No.: US 8,658,712 B2
(45) Date of Patent: Feb. 25, 2014

(54) METHODS OF TREATMENT OF THE DENTAL PULP AND FILLING ROOT CANALS USING WATER-BASED MATERIAL

(75) Inventors: Carolyn M. Primus, Bradenton, FL (US); James L. Gutmann, Dallas, TX (US); Miklos M. Breuer, Brookline, MA (US); Steven R. Jefferies, Media, PA (US)

(73) Assignee: Dentsply International Inc., York, PA (US)

( * ) Notice: Subject to any disclaimer, the term of this patent is extended or adjusted under 35 U.S.C. 154(b) by 468 days.

(21) Appl. No.: 12/069,359

(22) Filed: Feb. 8, 2008

(65) Prior Publication Data

US 2011/0104644 A1 May 5, 2011

Related U.S. Application Data

(60) Provisional application No. 60/900,475, filed on Feb. 9, 2007.

(51) Int. Cl.
| | |
|---|---|
| *A61L 24/02* | (2006.01) |
| *A61K 6/06* | (2006.01) |
| *A61K 6/02* | (2006.01) |
| *A61K 6/00* | (2006.01) |

(52) U.S. Cl.
USPC ........... 523/116; 523/113; 523/115; 433/224; 433/226; 433/228.1; 106/35

(58) Field of Classification Search
USPC .................. 523/116, 113, 115; 433/224, 226, 433/228.1; 106/35
See application file for complete search history.

(56) References Cited

U.S. PATENT DOCUMENTS

| | | | |
|---|---|---|---|
| 4,647,600 A | | 3/1987 | Kawahara et al. |
| 4,689,080 A | | 8/1987 | Kawahara et al. |
| 4,871,531 A | * | 10/1989 | Hartlaub et al. ............... 424/48 |
| 5,415,547 A | | 5/1995 | Torabinejad et al. |
| 5,454,867 A | | 10/1995 | Brothers et al. |
| 5,769,638 A | | 6/1998 | Torabinejad et al. |
| 6,566,418 B2 | * | 5/2003 | Imai et al. .................... 523/116 |
| 6,872,244 B2 | | 3/2005 | Kobayashi et al. |
| 7,303,817 B2 | | 12/2007 | Jia |
| 2002/0045678 A1 | * | 4/2002 | Lopez et al. ................. 523/116 |
| 2003/0159618 A1 | * | 8/2003 | Primus ........................... 106/35 |
| 2005/0222282 A1 | * | 10/2005 | Nyssen .......................... 521/58 |
| 2007/0098811 A1 | | 5/2007 | Lu et al. |

FOREIGN PATENT DOCUMENTS

| | | |
|---|---|---|
| EP | 0587383 | 3/1994 |
| WO | WO 2005/039509 | 5/2005 |
| WO | WO 2005039509 A1 * | 5/2005 |
| WO | WO 2005/087178 | 9/2005 |
| WO | WO 2007/051290 | 5/2007 |

OTHER PUBLICATIONS

Benjamin Ber, John Hatton, Gregory Stewart—"Chemical Modification of ProRoot MTA to Improve Handling Charateristics and Decrease Setting Time", Basic Research—Technology vol. xx No. x 2007.

Gian Pelliccinoni, Carlo Vellani, Maria Gatto, Maria Gandolfi, Claudio Marchetti, Carlo Prati—"ProRoot Mineral Trioxide Aggregate Cement Used as a Retrograde Filling without additional Water: As in Vitro Evaluation of Its Microleakage" Basic Research—Technology vol. xx No. x 2007.

J. Dustin Watts, Dennis Holt, Thomas Beeson, Timothy Kirkpatric, Richard Rutledge—Effects of ph. and Agents on the Temporal Setting of Tooth-Colored and Gray Mineral Trioxide Aggregate Basic Research—vol. xx No. x 2007.

Paul Vizgirda, Frederick Liewehr, Willaim Patton, James McPherson, T. B. Buxton—A Comparison of Laterally condensed Gutta-Percha, Thermoplasticized Gutta-Percha, and Mineral Trioxide Aggregate as Root Canal Filling Materials Journal of Endodontics—vol. 30, No. 2, Feb. 2004.

Yoshihiko Ohama—Polymer-based Admixtures Ciment and composites 20 (1998) 189-212.

\* cited by examiner

*Primary Examiner* — Michael Pepitone
(74) *Attorney, Agent, or Firm* — David Zdurne; Douglas Hura; Leana Levin

(57) ABSTRACT

Improved compositions comprising a mixture of particulate materials with water-based liquids containing water-soluble polymers and surfactants are provided. Examples of particulate powders include mixtures of calcium silicate, calcium aluminate, calcium sulfate, and hydroxyapatite. Examples of water-soluble polymers include polyvinyl alcohols, polyvinyl pyrrolidone, partially hydrolyzed polyvinyl acetates, polyacrylic acid, and polymethacrylic acid. Surfactants such as sodium dodecyl sulfate are added to the composition to interact with the polymeric materials. The compositions are particularly suitable for sealing and obturating dental root canals and root apices. The composition provides a stable barrier to bacterial and fluid leakage in the root canal system of a tooth. In addition, the compositions help promote the growth of new bone and tissue surrounding the root-tip area or dentin tissue that covers an injured or amputated pulp.

21 Claims, 2 Drawing Sheets

METHODS OF TREATMENT OF THE DENTAL PULP AND FILLING ROOT CANALS USING WATER-BASED MATERIAL

CROSS-REFERENCE TO RELATED APPLICATIONS

This application claims the benefit of U.S. Provisional Patent Application Ser. No. 60/900,475 having a filing date of Feb. 9, 2007, the entire contents of which are hereby incorporated by reference.

BACKGROUND OF THE INVENTION

1. Field of the Invention

The present invention relates generally to improved dental compositions for treating the pulp and root canals in a tooth. The compositions contain a mixture of particulate materials such as calcium silicate, calcium aluminate, calcium hydroxide, and hydroxyapatite; various organic water-soluble polymeric materials; and surfactants that interact with the polymeric materials.

2. Brief Description of the Related Art

The inner portion of a tooth includes a pulp cavity that contains soft living tissue or the "pulp" of the tooth. The pulp includes connective tissue, blood vessels, cells, and nerve endings. The pulp cavity comprises an upper pulp chamber and root canals that extend to the apex or apical section of the tooth deeper into the jaw. The outer (visible) portion of the tooth is referred to as the crown and has a covering of enamel. The hard enamel protects softer dentinal tissues in the upper portion of the tooth. The enamel consists of a hard, calcium-based substance, hydroxyfluorapatite. The dentin tissue contains a matrix of minute hydroxyapatite tubules interspersed with collagen fibers that surround and protect the tooth pulp. The outer (non-visible) portion of the tooth root is covered with cementum, a thin hard tissue that joins the root to the surrounding bone through Sharpey's fibers. Dental decay, or caries, is caused by bacteria accumulating on teeth and forming a biofilm (plaque). The biofilm produces acids that dissolve and weaken the hydroxyapatite of the tooth, thereby causing decay.

When dental caries are found in the enamel portion of a tooth, a dental professional will remove the caries to prevent further decay of the tooth. Then, the cavity is "filled" with a composite resinous material or amalgam filling. However, in some instances, the dental caries may be so deep that it penetrates to the dentin tissue. At this point, the bacteria and other microorganisms can migrate rapidly into the pulp tissue causing infection and inflammation. As a result, abscesses or inflammation may form in the pulp, and eventually in the periapical tissues surrounding the root apex. Provided that the dental disease is not too progressed, dental professionals will use root canal treatment procedures to remove the infected tissue from the tooth and replace it with an inert, biocompatible material. Otherwise, extraction of the tooth might be required.

The root canal system of a tooth is complex and many treatment methods can be used depending upon the condition of the patient and approach of the practitioner. In general, root canal treatment methods first involve drilling an opening in the crown of the tooth to provide access to the pulp cavity. Then, endodontic files are used to remove the pulp and clean and shape the root canals. The files are used with an irrigant. After using the files, an irrigant may be used to remove the smear layer created by the files. A sealer is coated on the wall of the root canals and then, the root canals are filled with a filling material. This sealing of the roots ideally prevents bacteria and other microorganisms from re-entering and causing infection of the living tissue surrounding the root tip. As a final step, the pulp chamber and opening in the crown of the tooth is sealed with a dental restoration such as a filling material. Preferably a permanent crown is placed over the opening in the tooth, such crowns being made of metal, porcelain-enameled metal, polymer-veneered metal, or ceramic. A post may be placed in the root for stability of the crown, although this is usually done after the root canal procedure, and before the crown is made.

One method for filling root canals involves using naturally occurring or synthetic gutta-percha, an isomer of rubber. Gutta-percha points having a tapered conical shape can be prepared, and these points can be fitted into the root canal. Historically, one older treatment method involves using single cones of gutta-percha. In this method, zinc oxide-eugenol cement sealer is first placed in the root canal. Then a single unheated cone of gutta-percha is fitted into the root canal. New techniques have been developed including cold lateral compaction, where multiple gutta-percha cones are compressed into the root canal after a root canal sealer is placed on the canal walls. More recently, procedures employing heated gutta-percha are being used that allow the gutta-percha to flow so that it can move into the minute intra-canal spaces, lateral canals, accessory canals, and other irregularities of the canals. One such technique uses a metal or plastic carrier coated with a layer of gutta-percha. The carrier includes a metal or plastic shaft with a distal tapered end that extends from a cylindrically shaped handle. The carrier transports the gutta-percha into the working length of the canal and compacts the gutta-percha into lateral and accessory canals. Once the carrier is stabilized in the canal, the upper handle portion and shaft is severed at a point level to the orifice of the canal using a dental bur or other sharp instrument. The lower portion of the shaft remains in the canal encased in the hardened gutta-percha. Other warm gutta-percha techniques include the compaction of gutta-percha that is extruded into the canal after a root canal sealer is placed. Combinations of cold and warm gutta-percha sealing techniques also can be used.

Other root canal treatment methods involve using portland cement to repair root defects such as iatrogenic perforations, or when apical surgery is performed to fill the root end. In general, portland cement contains a compound formed from calcia, silica, alumina, and iron oxide materials. Portland cement is commonly gray, but white versions, with lower iron content are known. The portland cement is combined with water to form a slurry-like composition that is introduced into the root canal defect. The composition solidifies to seal the canal. When portland cement materials are used to fill or seal the root canals, the cement particulates should have a small particle size. The fineness of a cement is represented by the surface area and one measurement thereof is the Blaine Number representing the ratio of the cement's particle surface area to its weight (square centimeters of surface per gram).

Torabinejad et al., U.S. Pat. Nos. 5,769,738 and 5,415,547 describe using a portland cement composition having a Blaine number in the range of 4,000 to 5,500 cm$^2$/gram for various surgical and non-surgical root canal treatment procedures including sealing root canals, performing apicoectomies, and repairing root canal perforations. The '738 and '547 patents disclose combining the portland cement with water to form a composition that is introduced into the root canal. There is no disclosure in the '738 and '547 patents for making a composition containing water-soluble polymeric materials, surfactants, and portland cement.

In addition to portland cements, other biomedical cements have been developed for medical and dental applications. For example, Lu et al., US Patent Application Publication US 2007/0098811 discloses a biomedical cement containing at least one phosphate compound and at least one calcium silicate compound that does not contain any aluminum or magnesium compounds. Preferably, the cement contains 45 to 80 weight percent calcium oxide; 10 to 35 weight percent silica; and 1 to 30 weight percent phosphate. Water-soluble polymeric materials are not added to the cement. Hydroxyapatite can be added to form hydroxyapatite/calcium silicate hydrate gel in situ at room temperature.

Kawahara et al., U.S. Pat. No. 4,647,600 discloses a dental cement that can be used for pulp-capping, base lining, root canal filling, and other applications. The composition is made of two parts. Part A comprises at least two powders—100 parts by weight of a powder containing calcium oxide and alumina; and 2 to 70 parts by weight of calcium hydroxide powder. According to the '600 patent, it is important that the powder particulates be surface-treated with organic and/or inorganic acids to increase the flowability of the particulate during mixing. Part B comprises an aqueous solution containing 0.01 to 70 wt. % of a water-soluble, high molecular weight substance (for example, polyvinyl pyrrolidone, polyethylene oxide, sodium polyacrylate, and sodium polymethacrylate.) Dental cements containing powder particulate, water-soluble polymeric materials, and surfactants are not disclosed in the '600 patent.

Kawahara et al., U.S. Pat. No. 4,689,080 discloses a composition of alumina cement that can be used in dental pulp capping, root canal filling, sealing, alveolar bone reconstruction, and the like. The alumina cement is an industrial cement that can be mixed with other materials. The composition consists of: a) industrial calcium aluminate powder; b) calcium type powder hardening retarder such as calcium hydroxide, calcium chloride, or calcium oxide; and c) water-soluble polymer such as polyvinyl alcohol, polyvinyl pyrrolidone, gum arabic, acrylic acid, glycerine, sodium metasilicate, low-molecular fatty acid, or hydrophobic natural resin. According to the '080 patent, it is important that a hardening retarder, preferably calcium hydroxide, be added to the mixture. The calcium hardening retarder is added in a ratio of 1-20 parts by weight to 100 parts by weight of alumina cement powder. Compositions containing powder particulate, water-soluble polymeric materials, and surfactants are not described in the '080 patent.

Jefferies and Primus, PCT International Application Publication No. WO 2005/087178 discloses a polymer-infiltrated structure of calcium-based cement that can be potentially used as a pulp capping agent, root repair material, root canal sealer, and other clinical products. A self-etching/self-priming dental adhesive can be applied to the surface of an unset dental cement material to form a polymer-infiltrated structure. The surface infiltration permits stabilization of the cement before it fully sets. In another example, a portland cement material is described as being mixed with a solution of 2-10% polyvinyl pyrrolidone having a molecular weight between 40,000 and 1,300,000. There is no disclosure of using any surfactants in the composition.

Another material that is used in surgical and non-surgical root canal procedures is ProRoot™ MTA root repair material available from Dentsply Tulsa Dental Specialties (Tulsa, Okla.). ProRoot MTA material has a composition similar to portland cement and does not contain any water-soluble polymeric materials. Particularly, the MTA material includes fine hydrophilic particles of dicalcium silicate, tricalcium silicate, tricalcium aluminate, tetracalcium aluminoferrite, calcium sulfate dihydrate, and bismuth oxide that are combined with water to form a cement-like material. The MTA material is available in gray and white colored formulations. The oxides used in the MTA powder are of the highest purity to ensure that no heavy metals are included and used in the body. MTA root canal repair material is used in a wide variety of clinical applications. Particularly, the cement-like material has been used to repair root canal perforations during root canal therapy; fill root ends; treat injured pulps in procedures known as pulp capping and pulpotomy, and repair root resorption.

Although MTA materials are generally effective in surgical and non-surgical root canal procedures, some dental literature has criticized these materials for having poor handling properties and a sand-like feel. There is a need for a composition having improved handling and placement properties. The composition should have good working time so that the dental practitioner can handle and place the material more effectively and preferably the material will start to set before the dental procedure is completed. Ideally, the material should promote the healing or repair of the pulp-tissue or the tissue surrounding root canal tips. The material should also provide a tight seal against the root canal dentin to prevent bacterial migration through the root canal. The present invention provides such improved materials.

SUMMARY OF THE INVENTION

The present invention provides improved compositions for treating the pulp and root canals in a tooth. The compositions can be used in various applications including the repair of root canal perforations, filling of root ends, treatment of injured pulps and repair of root resorption. In general, the compositions are made from a powdered particulate material and a liquid carrier comprising water-soluble polymers, surfactants and water. Various particulate material, polymeric materials, and surfactants can be used in accordance with this invention. For example, the particulate material can be selected from the group consisting of calcium silicate, calcium aluminate, tetracalcium aluminoferrite, calcium phosphate, calcium sulfate, silica, alumina, calcium oxide, calcium hydroxide, and mixtures thereof. The powdered particulate is optionally blended with hydroxyapatite, a form of calcium phosphate, and other compounds such as radiopaque materials. Preferably, the particulate has a surface area of at least $0.5 \text{ m}^2/\text{g}$ and more preferably greater than $0.9 \text{ m}^2/\text{g}$. Examples of suitable water-soluble polymeric materials that can used in the compositions include polyvinyl alcohols, polyvinyl-pyrrolidone (PVP), partially hydrolyzed polyvinyl acetates, (PVAc), polyacrylic acid (PAA), and polymethacrylic acid (PMA), and mixtures thereof.

Adding the surfactants is important, because they interact with the water-soluble polymers to form complexes that impart desirable rheological properties to the composition. Examples of suitable surfactants include sodium dodecyl sulfate (SDS)), fatty acid salts with $C_{10}$-$C_{24}$ side chains, (for example, sodium stearate), alkyl ether sulfates, alkyl sarcosinates, alkyl betaines, and other anionic, cationic, and non-ionic surfactants having alkyl side chains. Preferably, the ratio of surfactant to polymer in the composition is no greater than 6:1. The compositions of this invention have many advantageous properties. The growth of new bone and tissue surrounding the root tip is enhanced in cases where an infection is present. In addition, the biocompatible compositions provide a stable barrier to bacterial and fluid leakage in the root canal system of a tooth.

DETAILED DESCRIPTION OF THE PREFERRED EMBODIMENTS

The present invention provides new compositions suitable for use in healing diseased teeth. The compositions are particularly suitable for use in treating root canals. In addition, the compositions may be used for cavity lining or pulp-capping of carious teeth, treatment of traumatized teeth, or any procedure where bacterial leakage is to be minimized between the coronal and apical areas.

The composition of this invention is made from two parts. Part A of the product is particulate material selected from the group consisting of calcium silicate, calcium aluminate, tetracalcium aluminoferrite, calcium phosphate, calcium sulfate, silica, alumina, calcium oxide, calcium hydroxide and mixtures thereof. Such particulate materials and mixtures thereof may be referred to herein as "dentalcrete" particulate. The dentalcrete particulate can be optionally blended with hydroxyapatite, a form of calcium phosphate, particulate. Compositions containing a combination of dentalcrete and hydroxyapatite particulate may be referred to herein as "phoscrete" particulate. Other compounds such as bismuth oxide, barium sulfate, tantalum oxide, cerium oxide, tin oxide, zirconium oxide, and radiopaque glasses that contain lanthanide or actinide compounds, tantalum, barium or strontium can be blended with the dentalcrete powdered particulate to make the material more opaque to x-rays as discussed further below.

The particulate material must contain particles of suitable size. To create a fine-powdered material, the particulate can be subjected to conventional air and solid media attrition techniques. This increases the surface area of the particles and reduces the particle size. The powdered particulate used in the composition of this invention preferably has a surface area of equal to or greater than $0.5 \, m^2/g$ and more preferably greater than $0.9 \, m^2/g$. The particles generally have a surface area in the range of 0.5 to $3.0 \, m^2/g$ and more preferably 0.9 to $3.0 \, m^2/g$. In one preferred embodiment, the particle size of the powder is reduced so that the maximum and average diameter sizes of the individual particles fall below 40 µm, more preferably below 15 µm, and most preferably below 10 µm. In some instances, the particles may be so fine that they have an average particle size of less than 1 µm. The average particle size of the particulate is preferably in the range of 10 times smaller than conventional portland cement particulate. Industrial and construction grade cement contain particles having an average particle size that is too large for the compositions of this invention. There also tends to be substantial agglomeration and aggregation of particles in such industrial cements. In contrast, the powdered particulate used in the present formulation comprises discrete and individual particles, which are not substantially agglomerated or aggregated. These particles are characterized by having a small particle size and large surface area. The small, discrete individual particles in the composition provide several advantages over industrial cement particles.

For example, using such fine particles means that the hydraulic colloidal gel particles are more on a scale with dentinal tubules and lateral root canals in the tooth. The dentinal tubules in the root are microscopic, 1 to 3 inn in diameter, straight, and plentiful, with a density of 800 to 57,000 per square millimeter. Secondly, the fine particles can be blended easily and homogenously with the other ingredients of the composition. The small particles are mixed and distributed uniformly within the resin matrix. In contrast, the particles used in some traditional dental cements, for example, the cements described in the above-mentioned Kawahara et al., U.S. Pat. No. 4,647,600, must first be surface-treated with inorganic or organic acids before they are mixed with other components.

Using a powder particulate having such a small particle size significantly improves the viscosity and handling properties of the ultimate composition as discussed further below. The preferred powder comprises particulate selected from dicalcium silicate, tricalcium silicate, tricalcium aluminate, tetracalcium aluminoferrite, calcium phosphate, calcium sulfate dihydrate, silica, alumina, calcium oxide, and calcium hydroxide, and combinations thereof. The powder may contain different amounts of the calcium phases such as the following compounds (listed from most to least amount of calcium phases): tricalcium aluminate, dicalcium silicate, tricalcium silicate, tetracalcium aluminoferrite, calcium hydroxide, and calcium sulfate dihydrate.

The above-described particulate (dentalcrete) can be mixed with other particulate powders in accordance with this invention. In such instances, the particle size of each of the powdered materials should be substantially equal. All of the particles dispersed in the resin matrix should have substantially the same fineness. For example, in one preferred version, the particulate is mixed with hydroxyapatite to form phoscrete as discussed further below. In another preferred embodiment, the particulate is mixed with a finely ground radiopaque material such as bismuth oxide, tin oxide, tantalum oxide, zirconium oxide, barium sulfate, barium or strontium-containing glasses, or other high atomic number, non-toxic, metal compounds including the lanthanides and actinides. Using such radiopaque materials, which absorb x-ray radiation, makes the composition visible in dental x-rays. The composition, which replaces the removed tooth structure, is made visible in the x-ray images. This helps the clinician confirm that the composition has been correctly placed in the teeth after the pulp-capping, pulpotomy, non-surgical, or surgical root procedure.

To form a phoscrete mixture, hydroxyapatite, a calcium phosphate compound, is added to the mixture of calcium compounds in the dentalcrete. In general, autogenous bone has two basic components, organic and inorganic. The inorganic component of autogenous bone is primarily hydroxyapatite, and the organic component is primarily collagen. Hydroxyapatite powder is believed to help promote healing and repair of the bone and tissue surrounding the root tip, or in contact with dental pulpal tissue. Hydroxyapatite is compatible with the calcium compounds of dentalcrete and provides a stable, non-resorbable platform for bone and tissue repair. In the hydroxyapatite-containing dentalcrete composition of the present invention, the hydroxyapatite component has the same mineral composition as human bone, thereby providing a natural scaffold for bone and tissue regeneration. However, variations in the hydroxyapatite composition are equally suitable where the apatite is partially replaced by carbonate, or the hydroxyl is partially replaced by fluoride. Also, compositional variations with the calcium being partially replaced by strontium or barium are also in the spirit of the same invention. All of the compositions of this invention have good dimensional stability and will not cause expansion and stress on teeth, nor shrink to allow bacterial transit.

Part B of the product is a liquid carrier comprising water-soluble polymers, and surfactants, and water. By the term, "water-soluble polymer" as used herein, it is meant any substance of high molecular weight that swells or dissolves in water. The water-soluble polymer should be non-toxic and compatible with other components of the composition. Examples of suitable water-soluble polymers include, but are not limited to, non-ionic polymers such as, for example, polyvinyl alcohols (PVA) and its co-polymers, partially hydrolyzed polyvinyl acetates, (PVAc), polyvinyl-pyrrolidone (PVP), hydroxyethyl methacrylate (HEMA), water-soluble poly-saccharides (e.g. xanthan gum), polyethylene glycols and its water-soluble derivatives, polypropylene glycols and its water-soluble derivatives. Various water-soluble co-polymers containing the above residues also can be used. Additional examples of water-soluble polymers include anionic polymers such as, for example, polyacrylic acid (PAA), its water-soluble salts, derivative and copolymers, polymethacrylic acid (PMA) its water-soluble salts, derivatives and its water-soluble copolymers, water-soluble copolymers containing maleic acid residues, poly-glucuronic acid, polyglutamic acid its water-soluble salts, poly-aspertic acid and its water-soluble salts, hyaluronic acid and its water-soluble salts and derivatives, polystyrene sulfonates its salts and their copolymers.

In a preferred embodiment, the water-soluble polymer is selected from the group consisting of polyvinyl alcohols, polyvinyl-pyrrolidone (PVP), partially hydrolyzed polyvinyl acetates, (PVAc), polyacrylic acid (PAA), and polymethacrylic acid (PMA), and mixtures thereof. Preferably, the molecular weight of the water-soluble polymer is in the range of 20,000 to 2,000,000. More preferably, the molecular weight of the water-soluble polymer is in the range of 80,000 to 2,000,000. Preferably, the concentration of water-soluble polymer is in the range of about 5% to about 40% by weight based on weight of the composition.

The surfactants used in the composition should be medically acceptable and suitable for use in dental applications. Adding the surfactants improves stability and handling properties. The surfactants interact with the water-soluble polymers to form complexes that impart desirable rheological and other physical properties to the composition. Particularly, the resulting composition has a more "elastic" and "string-like" consistency when mixed with a powder. Importantly, the interaction of the surfactants with the water-soluble polymers helps improve the elasticity of the composition when mixed with the powder. This means that the composition can be used like other resinous root canal materials. Furthermore, due to accelerated setting by the polymers, the mixed material will not wash away easily from the localized treatment area. Examples of suitable surfactants include, but are not limited to, alkyl sulfates (for example, sodium dodecyl sulfate (SDS)), fatty acid salts with $C_{10}$-$C_{24}$ side chains, (for example, sodium stearate), alkyl ether sulfates, alkyl sarcosinates, alkyl betaines, and other anionic, cationic, and non-ionic surfactants having alkyl side chains suitable for human use. In a preferred embodiment, the surfactant is selected from the group consisting of alkyl sulfates, alkyl ether sulfates, and sarcosinates, and mixtures thereof. Preferably, the concentration of surfactant is in the range of about 1% to about 40% by weight based on weight of the composition. The ratio of surfactant to polymer should be no greater than 6 to 1. In one preferred embodiment, the ratio of surfactant to polymer in the composition is 3:1 or less, and more preferably 0.5:1.

Various additives such as, for example, plasticizers, softening agents, humectants, stabilizers, and anti-bacterial agents also can be added to the mixture. However, as opposed to some traditional cement materials, which require the addition of a calcium-type powder hardening agent such as calcium hydroxide, there is no need to add such hardeners to the composition of this invention. Calcium hydroxide particulate optionally can be added to the instant formulation, but it is not required. Rather, the formulation, by and in itself as described herein, has sufficient strength and other desirable properties. Of course, it should be understood that calcium hydroxide may form as a reaction product when the powdered particulate is mixed and reacted with the liquid carrier. For example, the powdered particulate may contain particles of tricalcium silicate, dicalcium silicate, and tricalcium aluminate hydrate. When these compounds react with water, they produce several reaction products including calcium hydroxide.

In practice, clinicians can dispense the powdered material (Part A) onto a pad; add the liquid carrier (Part B); and mix the components together using a spatula to form the composition of this invention. The concentration of powder particulate in the composition is generally in the range of about 1 to about 80 weight percent, and the concentration of liquid carrier is generally in the range of about 1 to about 50 weight percent. To prepare a surgical or repair composition the particulate powder is preferably mixed with the liquid carrier in a ratio of three (3) to one (1). That is, in one preferred embodiment, the composition contains about 75 weight percent particulate and 25 weight percent liquid carrier. In other instances, the particulate powder can be mixed with the liquid carrier in different ratios such as, for example, four (4) to one (1) or five (5) to one (1). If the composition is intended to be used as a root canal sealer, the powder and liquid are preferably mixed in a ratio in the range of 1:1 to 2.5:1. In the final composition, the water content is generally in the range of about 1 to about 50 weight percent, preferably 15 to 30 and the water-soluble polymer is generally present in an amount of about 1 to about 50 weight percent, preferably 5 to 40 weight percent. If hydroxyapatite is present, it is preferably in a concentration of about 1 to about 30 weight percent. If a radiopaque component is present, it is preferably in a concentration of about 1 to about 60 weight percent.

Upon mixing the particulate powder with the liquid carrier, the particles, which are hydrophilic, react with the liquid to form hydrates. For example, the particulate powder preferably contains particles of tricalcium silicate, dicalcium silicate, and tricalcium aluminate. When these compounds react with water, they produce tricalcium silicate hydrate, dicalcium silicate hydrate, calcium hydroxide, and tricalcium aluminate hydrate. Each mineral compound reacts at a different rate. For example, the tricalcium silicate reacts relatively quickly, while dicalcium silicate hydrates more slowly. The material produced from the hydration reaction is a colloidal hydrate gel. Preferably, the particles dispersed in the gel have a very small particle size as discussed above. The product begins to harden and will eventually solidify to form a material having high compressive strength where the particles are mostly hydrated. Because the mixed material has good resistance to washout and displacement, the particulate material can react with the water and form a mass of relatively high compressive strength (>30 MPa) in situ. The material is able to resist washing out when the root canal system is rinsed with water, or other fluid to complete a surgical procedure.

The surfactants interact with the water-soluble polymers to form complexes. As the surfactants interact with the polymer, the rheology and other physical properties of the polymers change. In turn, the composition develops favorable properties; particularly, the handling and placement properties of the composition are enhanced. The dental clinician can work with and handle the hydrated gel more efficiently before it sets to form a rock-like substance in the root canal. Particularly, the composition has suitable rheological properties (for example, viscosity, setting time, elasticity, consistency, and the like) so it can be effectively used for treating vital and non-vital teeth. Good elasticity is very important for root canal sealers. The composition has good stability and holds the particulate in place, which is very important for surgical procedures. In general, the combinations of powder and liquid carrier compositions have either a putty-like or syrup-like consistency as discussed further below.

It should be understood that mixing the powdered material with a liquid carrier (containing water-soluble polymer, surfactant, and water) as described above is but only one possible method of preparing the composition of this invention. Other methods can be used. For example, Part A can be prepared by blending the powdered particulate with the surfactant and Part B can be prepared by dissolving the polymer in water. Then, Parts A and B can be combined to form the composition that will be used in dental therapy. Another technique involves mixing the powdered particulate with water (Part A) and then combining this mixture with a previously prepared mixture of water-soluble polymer and surfactant (Part B).

In some root canal treatment cases, gutta-percha and root canal sealer materials can be extruded beyond the apex of a tooth. These materials can be irritants and cause residual discomfort until the body reabsorbs or encapsulates the material over a period of months or years. The compositions of this invention have good biocompatibility with the root canal system and promote normal healing of the bone and tissue surrounding the root tip, particularly if any of the material is extruded beyond the apex. The composition enhances the growth of new bone and tissue surrounding the root tip if an infection was present and is anti-microbial when it makes contact with bacteria. Adding the bioactive hydroxyapatite powder further enhances these phenomena to promote growth of cementum or reparative dentin, depending upon the application of the material.

The improved compositions of this invention provide enhanced bonding to gutta-percha and to dentin. Bonding of sealer to dentin or gutta-percha has been a topic of great concern to endodontists in the prevention of bacterial migration in obturated, root-canal-treated teeth. The hydrophilic nature of the calcium silicate and calcium aluminate compounds enhances the reactivity of the composition of the present invention with moist dentin. In addition, the formulations of the present invention have enhanced bonding to gutta-percha, owing to the presence of the hydrophobic side chains in the partially hydrolyzed polyvinyl acetate and/or other polymers used. The hydrophobic side-chains have an affinity for gutta-percha. Because of their improved bonding properties, the composition provides an improved barrier to bacterial and fluid leakage in the root canal system of a tooth. The composition effectively seal offs communication pathways from the coronal to the apical portions when used as a root canal sealer, obturation material, root-end filling, apexification, perforation repair, or root resorption. As a result, bacterial migration into the root canal system is reduced or prevented.

The improved compositions of this invention can be either putty-like or syrupy in viscosity. When the composition is in the form of a putty-like material, it can be used in root canal indications such as apicoectomies, apexification, perforation repair, obturation, pulpotomies, or root-resorption repair. When the composition is in the form of an elastic material having a honey-like consistency, it can be used for root canal sealing or perhaps obturation. The rheological properties (viscosity, elasticity, and the like) of the powder-liquid combination are determined by the particle size distribution of the powder, the composition of the liquid, and the powder to liquid ratio. Finer powders; more viscous liquids; more polymers; and a higher powder to liquid ratio all make a more putty-like material used for pulp-capping, cavity liner, root-end filling, obturation, pulpotomies, apexification, or treating perforations or root resorption. The composition of this invention is introduced into the tooth from the coronal or apical openings.

For example, the compositions can be used to seal at least a portion of the tooth; repair root perforations; repair root resorption; fill root ends; and cap at least a portion of the dental pulp that has been exposed. The composition also can be used to line a cavity preparation where pulp-exposure is possible. Moreover, complete obturation of root canals can be performed using the material of this invention. In addition, after a pulpotomy has been performed, the composition can be used to cover a root access opening in a root. In yet another example, the composition can be used to seal a root canal after gutta-percha has been introduced into the canal.

The invention is further illustrated by the compositions described in the following Examples, but these Examples should not be construed as limiting the scope of the invention.

EXAMPLES

Example A

A root canal sealer was formulated with dentalcrete having 40 wt. % bismuth oxide and 60 wt. % of a mixture of calcium silicates, calcium aluminate, and calcium sulfate. (The approximate composition was 73 wt. % tricalcium silicate, 17 wt. % dicalcium silicate, 5 wt. % tricalcium aluminate, 1 wt. % tetracalcium ferrite, and 4 wt. % calcium sulfate.) The liquid carrier mixed with this powder contained 5 wt. % partially hydrolyzed polyvinyl acetate, 15 wt. % sodium n-dodceyl sulfate and 80 wt. % water. The resulting root canal sealer formulation is identified as "Experimental MTA" in this Example A and in FIG. 1.

The microleakage (hydraulic conductance) of root canal systems (human teeth) sealed with Experimental MTA was tested in vitro. Cleaning and shaping of the teeth as well as canal obturation were performed under an operating microscope (OPMI pico, Carl Zeiss Surgical, Inc., Thornwood, N.Y.). Detailed radiographic documentation of the pre-operative specimens, working lengths, cone-fit, post-operative condition of the root fillings. For each root segment, canal patency was achieved using ISO size #15 Flex-o-file (Dentsply Tulsa Dental Specialties). The working length was established at 1 mm short of the apex. Cleaning and shaping of the root canals was performed with a crown-down technique, using size 2-4 Gates Glidden drills and Profile nickel-titanium rotary instruments (Dentsply Tulsa Dental Specialties). All canals were prepared to ISO size 40, 0.06 taper. To ensure optimal cutting efficacy, a new set of rotary instruments was used for the shaping of two roots.

Experimental Group—Ten teeth were randomly selected for the experimental group. Canals were irrigated between instrumentation with 5 mL of 1.3% sodium hypochlorite (NaOCl) delivered to within 2 mm of the working length using BioPure™ MTAD irrigation needles (ProRinse Needles; Dentsply Tulsa Dental Specialties). For each root canal, 5 mL of BioPure MTAD root canal cleanser solution (Dentsply Tulsa Dental Specialties) was used for 5 min after the completion of instrumentation and as the final rinse prior to root canal obturation, according to the manufacturer's instructions. The debrided root canals were dried with multiple paper points (Lexicon AP0640, Dentsply Tulsa Dental Specialties). A size #40 Lexicon 0.06 taper gutta-percha master cone (Dentsply Tulsa Dental Specialties) was tried-in to within 1 mm of the working length, with additional trimming if necessary to achieve tug-back. Cone-fitting was confirmed radiographically prior to root canal obturation. The experimental root canal sealer composition of this invention was freshly mixed for each root canal obturation by mixing the powder and the liquid uniformly into a homogenous mix at a ratio of 2:1 powder to liquid. The mixed experimental root canal sealer was introduced into the root canal with the master gutta-percha cone and spread as evenly as possible along the root canal walls.

Control Group—Ten teeth were randomly selected for the control group. Each canal was irrigated between instrumentation with 5 mL of 2.6% sodium hypochlorite (NaOCl) delivered to within 2 mm of the working length using the ProRinse irrigation needles (Dentsply Tulsa Dental Specialties). Five mL of 17% (0.5M; pH=7.4) ethylenediamine tetraacetic acid (EDTA) were used for 1 min after the completion of instrumentation and as the final rinse prior to root canal obturation. The debrided root canals were dried with multiple paper points (Lexicon AP0640, Dentsply Tulsa Dental Specialties). As with the experimental group, a size #40 Lexicon 0.06 taper gutta-percha master cone (Dentsply Tulsa Dental Specialties) was tried-in to within 1 mm of the working length, with additional trimming if necessary to achieve tug-back. Cone-fitting was also confirmed radiographically prior to root canal obturation.

A comparative Pulp Canal Sealer (zinc oxide eugenol sealer having a powder base and liquid catalyst), available from Kerr Corp. (Orange, Calif.) was mixed according to the manufacturer's instructions and introduced into the root canals of the control group teeth with master gutta-percha cones.

Control & Experimental: The root canals were similarly obturated with the continuous wave condensation technique using the System B heat source at 200° C. and then backfilled with the Calamus Flow Obturation Delivery System (Dentsply Tulsa Dental Specialties) using the 23 gauge Calamus™ Flow Singles gutta-percha cartridges.

Testing—The filled specimens from both the experimental and the control groups were stored for seven days at 37° C. and 100% relative humidity to allow the sealers to set. Leakage of the filled roots in each group (N=10) was evaluated using a modified fluid filtration study design that represents a modification of the previously reported protocol by Pashley and Depew. (Pashley D H, Depew D D. Effects of the Smear Layer, Copalite and Oxalate on Microleakage, Oper Dent 1986; 11:95-102.)

Briefly, a Plexiglas connection platform was first constructed by inserting a short length of an 18-gauge stainless steel tubing into a center hole created in a 2×2×0.6 cm piece of Plexiglas. The tubing protruded 1 mm from the top of the Plexiglas. A 2 mm deep cavity was then created from the coronal end of each root segment using a slow speed tungsten carbide bur. This modified technique created a reservoir for the insertion of the protruded metal tubing. The rationale for this modified protocol is based on the results obtained from a recently conducted pilot study that this technique eliminated clogging of the metal tubing and prevented the generation of false negative results. The tooth segment was attached to the Plexiglas platform and sealed with a cyanoacrylate adhesive, (Zapit, Dental Ventures of America, Inc., Anaheim Hills, Calif.). Each filled root was cemented with Zapit to the Plexiglas platform so that the coronal root canal orifice was centered over the orifice of the metal tubing. A radiograph was then taken of the attachment of the root segment to the fluid filtration device to ensure that the metal tubing was corrected inserted into the reservoir created along the coronal part of the root segment.

To measure microleakage, each Plexiglas-root assembly was attached to a fluid filtration apparatus as described previously by Derkson et al. and modified by Wu et al. (Wu M K, de Gee A J, Wesselink P R, Moorer W R. Fluid Transport and Bacterial Penetration Along Root Canal Fillings, Int Endod J 1993; 26:203-8. Polyethylene tubing (Fisher Scientific, Pittsburgh, Pa.) was used to connect the pressure reservoir to a 25 µL micropipette (Microcaps, Fisher Scientific). Additional tubing was used to connect the micropipette to a micro syringe (Gilmont instruments, Inc., Great Lakes, N.Y.) and the Plexiglas with the attached root. A small (1 to 2 µL) air bubble was subsequently introduced into the system with the micro-syringe and advanced into the micropipette. A pressure of 69 kPa (i.e. 10 psi) was then applied via the use of nitrogen gas to a phosphate buffer containing reservoir inside a modified pressure cooker. The phosphate buffer was forced through the voids along the root canal filling, displacing the air bubble in the micropipette. Quantification of the fluid flow per unit time was performed by observing the movement of the air bubble in the micropipette. Linear movement of the air bubble in millimeters was recorded after 10 min of equilibration of the fluid filtration system to enable complete relaxation of the stretched polyethylene tubing. Linear fluid movement within the micropipette was conducted for a period of 15 min and expressed as mm/min. Three of these 15-min measurements were performed for each root segment, from which the mean linear fluid movement was derived. The mean fluid flow rate of each root segment was calculated by multiplying the mean linear fluid movement by the internal bore diameter of the micropipette (0.386 mm$^2$) and expressed as $\mu L\ min^{-1}\ 69\ kPa^{-1}$.

Determination of Fluid Flow Rate for the Positive and Negative Controls

The protocol described above was employed for the determination of the fluid flow rates in the negative control group and the second positive control group. For the first positive control group (i.e. unfilled root canals), a modification of the protocol was necessary as the extremely rapid fluid movement did not permit the recording of linear fluid movement by following the bubble within the micropipette. Accordingly, a pre-weighed plastic beaker was placed over the apex of the root segment in this group, after the latter was connected to the fluid filtration apparatus. The phosphate buffer that was expressed through the root apex was collected in the plastic beaker. The time for the recording was also reduced from 10 min to 1 min. The weight of the water that was collected during the one minute period at 69 kPa pressure was converted into volume (mL). The flow rates in the first positive control group were similarly expressed as $\mu L\ min^{-1}\ 69\ kPa^{-1}$.

Data Treatment and Statistical Analysis

The 10 psi pressure was converted into cm water pressure (705 cm) and the mean fluid flow rates (i.e. hydraulic conductance) in all groups were expressed in $\mu L min^{-1} cm H_2O^{-1}$. The hydraulic conductance data from the experimental group and the control group were statistically analyzed.

Figure 1:
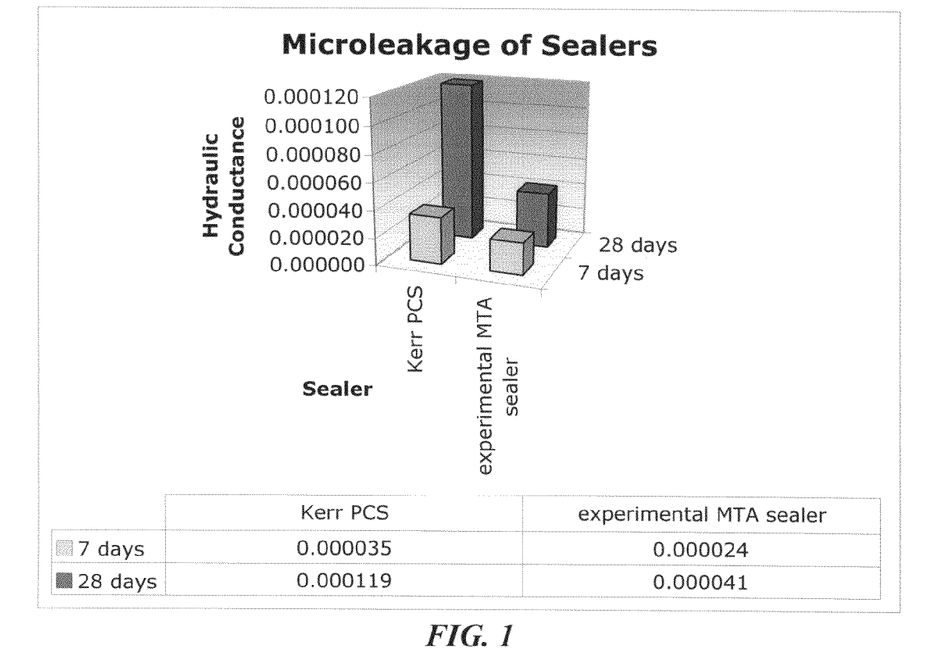
FIG. 1 is a bar graph showing fluid microleakage data in root canal systems treated with a first composition of this invention versus a comparative root canal sealer material.

A summary graph is provided in FIG. 1. As shown, the microleakage of the experimental MTA sealer with gutta-percha was not statistically different from the control (master cone of gutta-percha with Kerr's Pulp Canal Sealer). However, when an outlying data point from each group was removed, the hydraulic conductance of the control material was much greater at 28 days than the new root canal sealer composition of this invention. The composition of this invention (Experimental MTA) is thus more effective in sealing the root canal. The composition is capable of forming a barrier that resists fluid permeation into the canal. The composition can seal off fluid pathways between the root canal system and surrounding tissue.

Example B

The powdered particulate material described in Example A was used with various liquid carriers to prepare the compositions in this Example B. Particularly, the powder was mixed with the liquids listed in the following Table 1 to prepare various compositions. The concentration of powder in the composition was in the range of about 67 to about 80% by weight. When the powder was mixed with about 20% liquid, a putty-like composition was obtained. This composition could be used for root canal obturation, root-end repair, perforation repair, or other procedures. The sodium n-dodecyl sulfate improved the handling, but didn't accelerate the setting. The polyvinyl acetate may inhibit the setting when used alone. The combination of PVA with SDS, created the elasticity desired for some dental uses. The resulting mixtures were resistant to washout with a stream of water and hardened quickly enough to allow a clinician to proceed with covering the site and finishing the procedure. Various viscosities were obtained, but it is believed that each of the prepared compositions would be satisfactory for use in root canal obturation, root-endroot-end repair, and perforation repair. When about 33% liquid was added, an elastic consistency was obtained, and the composition was suitable for use as a root canal sealer material.

Surprisingly the combination of polyvinyl alcohol or hydrolyzed polyvinyl acetates and sodium n-dodecyl sulfate had synergistic effects; when a liquid carrier containing these ingredients was mixed with the powders, the resulting composition had an elastic consistency that allowed the material to be used as a root canal sealer. This combination of water-soluble polymers also reduced the apparent setting time and increased the washout resistance of the powder/liquid mixture. Separately, neither polymer in water was as satisfactory. Various polyvinyl alcohols were tested and all made a suitable mixture of varied viscosity. The partially hydrolyzed polyvinyl acetate was as viable as the fully hydrolyzed polyvinyl alcohol. The best liquid carrier combination was that of Sample 4 where the ratio of surfactant to water-soluble polymer was 6 to 1.

Example C

In this Example C, the powdered particulate material described in Example A was used, and different liquid carriers were tested as shown in Table 2. The concentration of powder in the composition was in the range of about 67 to about 75% by weight. The viscosities varied among these samples, but each sample was satisfactory for dental applications. The Steol material was a suitable substitute for the sodium n-dodecyl sulfate. Polyvinyl pyrrolidone was also a suitable material to use instead of polyvinyl acetate. However, when used alone, the polyvinyl pyrrolidone did not create an elastic mixture, although the setting was accelerated and seemed to add early strength to the mixtures.

TABLE 2

Example C:
Liquid Carriers 1-4 (Concentration of Components by Weight %)

| Component | 1 | 2 | 3 | 4 | 5 | 6 | 7 | 8 | 9 |
|---|---|---|---|---|---|---|---|---|---|
| Water | 92.5 | 92 | 91.5 | 89 | 96 | 92 | 90 | 81.7 | 83 |
| Steol CA-460 | 5 | 5 | 5 | 4 | | | | | |
| Ammonium laureth sulfate | | | | | | | | | |
| Polyvinyl acetate 87 to 89% hydrolyzed | 2.5 | 3 | 3.5 | 7 | | | | | |
| Sodium n-dodecyl sulfate | | | | | | | | | 10 | 5 |
| Polyvinyl pyrrolidone | | | | | 4 | 8 | 10 | 8.3 | 10 |

Example D

The powdered particulate material described in Example A was used to prepare the compositions in this Example D. Different liquid carriers containing the organic components listed in Table 3 were tested. The concentration of powder in the composition was in the range of about 67 to about 75% by weight. These liquids enabled the powder to set, but were less resistant to washout when mixed with dentalcrete by a stream of water than those liquids in Examples A, B, and C.

TABLE 1

Example B:
Liquid Carriers 1-24 (Concentration of Components by Weight %)

| Component | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| Water | 95 | 89.3 | 90 | 82.5 | 87.5 | 92.5 | 88 | 81 | 80 | 78 | 65 | 75 | 65 | 95 | 92.5 | 90 | 93 | 90 | 90 | 80 | 70 | 80 | 60 | 70 |
| Polyvinyl acetate 100% hydrolyzed 87,000 to 97,000 ave mole wt. | 4 | 7.1 | | 2.5 | 2.5 | 2.5 | 2 | | | | | | | | | | | | | | | | | |
| Polyvinyl acetate 87 to 89% hydrolyzed; 87,000 to 97,000 ave mole wt. | | | | | | | | 4 | 5 | 7 | 5 | 5 | 5 | 5 | 7.5 | 10 | | | | | | | | |
| Polyvinyl acetate 75% hydrolyzed; <80,000 mole wt. | | | | | | | | | | | | | | | | | 5 | 10 | 10 | 20 | 30 | | | |
| Sodium n-dodecyl sulfate | 1 | 3.6 | 10 | 15 | 10 | 5 | 10 | 15 | 15 | 15 | 30 | 20 | 30 | | | | | | | | | 20 | 40 | 30 |
| Chlorhexidine gluconate | | | | | | | | | | | | | | | | | 2 | | | | | | | |

TABLE 3

Example D:
Liquid Carriers 1-9 (Concentration of Components by Weight %)

| Component | 1 | 2 | 3 | 4 | 5 | 6 | 7 | 8 | 9 |
|---|---|---|---|---|---|---|---|---|---|
| Water | 88 | 96 | 90 | 82 | 95 | 96.5 | 90 | 88 | 78 |
| Sodium polyacrylate (low molecular weight) | 5 |  | 10 |  | 5 | 3.5 | 5 | 5 | 10 |
| Sodium polyacrylate (high molecular weight) |  | 2 |  |  |  |  |  |  |  |
| Polyvinyl acetate 87 to 89% hydrolyzed, average molecular weight 88,000 to 97,000 | 5 |  |  | 5 |  |  |  | 2 | 4 |
| Sodium n-dodecyl sulfate |  |  |  | 10 |  |  | 5 | 5 | 8 |
| Chlorhexidine gluconate | 2 | 2 |  | 2 |  |  |  |  |  |
| Polyvinyl acetate |  |  |  | 1 |  |  |  |  |  |

Example E

In this Example E, the powdered particulate material described in Example A was used. Different liquid carriers containing the organic components listed in Table 4 were tested. The concentration of powder in the composition was in the range of about 67 to about 75% by weight. The components included polyvinyl pyrrolidone and glycerol. These glycerol compounds retarded the setting of the powder so much that the materials could not be used appropriately.

TABLE 4

Example E:
Liquid Carriers 1-9 (Concentration of Components by Weight %)

| Component | 1 | 2 | 3 | 4 | 5 | 6 | 7 | 8 | 9 |
|---|---|---|---|---|---|---|---|---|---|
| Water | 57.5 | 60 | 48 | 43.7 | 57.5 | 80 | 20 | 50 | 84 |
| Polyvinyl pyrrolidone, molecular weight 1,300,000 |  |  |  |  |  |  |  |  | 7 |
| Polyvinyl acetate 87 to 89% hydrolyzed, average molecular weight 88,000 to 97,000 | 5 |  |  | 6.3 | 2.5 |  |  |  | 6 |
| Sodium n-dodecyl sulfate | 10 | 10 | 28 | 12.5 |  |  |  |  | 3 |
| Chlorhexidine gluconate | 2 |  |  |  | 10 |  |  |  |  |
| Cocoamidopropyldimethyl betaine | 0.5 |  |  |  |  |  |  |  |  |
| Glycerol | 25 | 30 | 24 | 37.5 | 30 | 20 | 80 | 50 |  |

Composition 9 in above Table 4, which did not contain glycerol, was tested for its microleakage and found to be equal to or superior to conventional materials used for root-end fillings during endodontic surgery. This composition is referred to as "Phoscrete" in this Example E and in FIG. 2. Leakage was compared with two commercially-available, frequently advocated root-end filling materials, White ProRoot MTA (Dentsply Tulsa Dental Specialties) and Super EBA (Bosworth Company, Skokie, Ill.).

In the test procedure, cleaned and shaped single-rooted teeth were filled with single gutta-percha cones without sealers, and severed at their root ends. Forty-two recently extracted human single-rooted teeth were stored until use in 0.9% NaCl solution containing 0.02% sodium azide to prevent bacterial growth. Instrumentation was performed with a crown-down technique using ProTaper nickel-titanium rotary instruments (Dentsply Tulsa Dental Specialties) until 1 mm of a F3 ProTaper file tip extruded beyond the apical foramen. The canals were rinsed with 10 mL of 6.15% sodium hypochlorite in between instrumentation followed by the use of 5 mL of 17% ethylenediamine tetraacetic acid as the final rinse. The apical 3 mm of each instrumented root was resected with a 10 degree bevel to its longitudinal axis. Root end preparations were made to a depth of 3 mm using ultrasonic tips.

Figure 2:
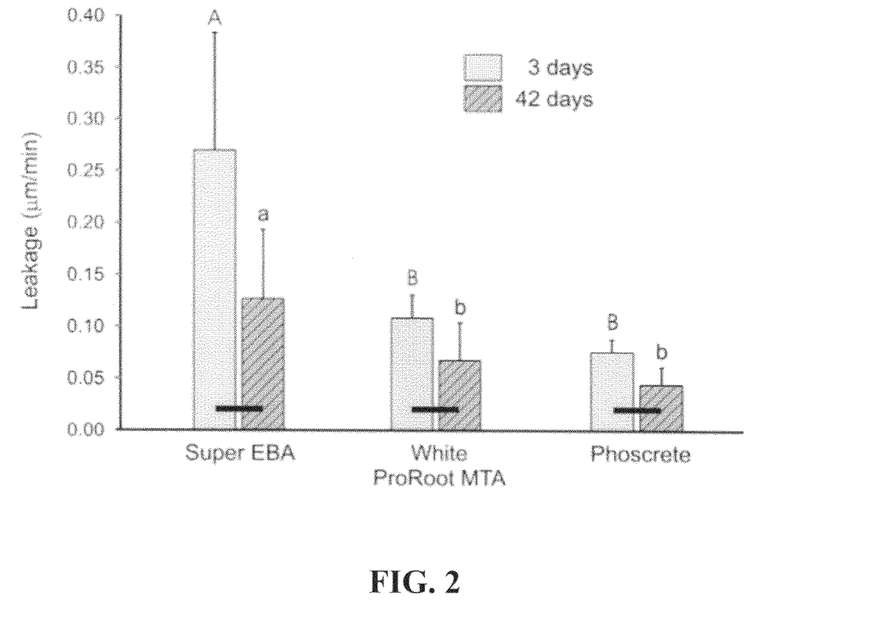
FIG. 2 is a bar graph showing fluid microleakage data in root canal systems treated with a second composition of this invention versus comparative root canal sealer materials.

The mixed materials were compacted into the root end preparations using microsurgical pluggers and the filled teeth were placed inside a humidor at 37° C. and 100% relative humidity for 24 hours and then stored in a separate scintillation vial containing 10 mL of phosphate-buffered saline. The teeth were aged in phosphate-buffered saline. Leakage was evaluated at 3 and 42 days. Leakage of the root-end fillings was evaluated using a fluid filtration design. Quantification of the fluid flow (μL/min) was performed by monitoring the displacement of a water bubble inside the glass capillary tube of a Flodec device via a light-sensitive photodiode. Data collection was performed every 1.04 sec using the Flodec software and the results are shown in FIG. 2. For the 3-day testing period, differences between materials that have the same upper case letter designations (e.g., B and B) are not statistically significant ($p>0.05$). For the 42-day testing period, differences between materials that have the same lower case letter designations (e.g., b and b) are not statistically significant ($p>0.05$). For each root-end filling material, before and after subgroups that are linked by a black horizontal bar indicate significant differences in fluid leakage ($p<0.05$).

For both testing periods, leakage in the Super EBA group was significantly higher than the other two groups (White ProRoot MTA and Phoscrete experimental sealer of this invention in FIG. 2.), which were not different from each other. For each material, leakage at 42 days was significantly lower than the leakage at 3 days. The experimental root-end filling Phoscrete material created an excellent seal.

Example F

The powdered particulate material described in Example A was used in this Example F. The concentration of powder in the composition was in the range of about 67 to about 75% by weight. Different liquid carriers containing different organic components as listed in Table 5 including: polyvinyl pyrrolidone, polyvinyl alcohol, polyvinyl acetate, and sodium n-dodecyl sulfate were tested. These liquids enabled the powder to set, and were very resistant to washout by a stream of water. Surprisingly, the combinations were more resistant to washout than any of the materials tested individually.

TABLE 5

Example F:
Liquid Carriers 1-9 (Concentration of Components by Weight %)

| Component | 1 | 2 | 3 | 4 | 5 | 6 |
|---|---|---|---|---|---|---|
| Water | 80 | 82 | 83 | 84 | 83 | 82 |
| Polyvinyl pyrrolidone, molecular weight 1,300,000 | 7 | 7 | 7 | 7 | 7 | 7 |
| Polyvinyl acetate 87 to 89% hydrolyzed, average molecular weight 88,000 to 97,000 | 10 | 8 | 7 | 6 | 6 | 6 |
| Sodium n-dodecyl sulfate | 3 | 3 | 3 | 3 | 3 | 3 |
| Chlorhexidine gluconate | | | | | 1 | 2 |

The liquid carriers having the components described in Table 5 appear to be the most preferred liquids for mixing with the particulate powders to make the compositions of this invention. It has been found that the concentration of components in the liquids can be adjusted as shown, for example, in Table 5, and the resulting compositions are suitable for use in various endodontic indications. These applications include, for example, root canal sealing, root canal obturation, root repairs, and vital pulp therapy.

Example G

In this Example G, different powdered particulate materials were prepared and tested. The Example G powders differed from the powder described in Example A by the addition of different polymers. Water was added to the Example G powders. The below Table 6 describes the components in more detail. It was found that the resulting compositions of Example G had inferior handling and setting properties as compared to the compositions of Example F.

TABLE 6

Example G:
Compositions 1-5 (Concentration of Components by Weight %)

| Component | 1 | 2 | 3 | 4 | 5 |
|---|---|---|---|---|---|
| Dentalcrete | 97 | 92 | 98 | 92 | 86 |
| Sodium n-dodecyl sulfate | 3 | 8 | | | |
| Sodium polyacrylate | | | 1 | 7 | 7 |
| Xanthan gum | | | 1 | 1 | 7 |

Example H

In this Example H, the powder component was modified to include hydroxyapatite or calcium sulfate. The liquid carriers of Example F were used with the powder. In particular, the liquids were mixed with the powder in a powder to liquid ratio of 4 to 1 (80% powder). The combination of Liquid Carrier No. 4 (Example F) with Powder Mixture No. 1 in Table 7 below was a preferred composition in this Example. The consistency of the composition was putty-like. The radiopacity of the composition was equal to 9 to 10 mm of aluminum, measured per the method in ISO 6876.

TABLE 7

Example H:
Particulate Powders 1-3 (Concentration of Components by Weight %)

| Component | 1 | 2 | 3 |
|---|---|---|---|
| Calcium silicate & calcium aluminates | 56 | 56 | 59 |
| Bismuth oxide | 36 | 36 | 36 |
| Calcium sulfate | | 10 | 5 |
| Hydroxyapatite | 10 | | |

Example I

In this Example I, the powder component described in Example A was used. The liquids described in Table 8 below were mixed with the powder. The silica sol improved the handling of the composition, but did not speed the setting. The potassium carbonate accelerated the setting of the compositions, but the washout-resistance of the composition was not as strong as desired. Rinsing is used in dentistry to clean a surgical site or an area of blood before a site is closed. This is usually done with sterile water or sterile solution. Thus, it is important that the compositions have good washout-resistance so that it will not rinse away.

TABLE 8

Example I:
Liquids Carriers 1-3 (Concentration of Components by Weight %)

| Component | 1 | 2 | 3 |
|---|---|---|---|
| Water | 97.5 | 98 | 80 |
| HEMA | | | |
| Potassium Carbonate | 2.5 | 2 | |
| Silica Sol | | | 20 |

Example J

In this Example J, various organic components, as described in Table 9, were added to the powdered particulate (described in Example A) and mixed with water to prepare the compositions.

TABLE 9

Example J:
Compositions 1-9 (Concentration of Components by Weight %)

| Component | 1 | 2 | 3 | 4 | 5 | 6 | 7 | 8 | 9 |
|---|---|---|---|---|---|---|---|---|---|
| Water | 23 | 30 | 25.1 | 23 | | | | 24 | 26 |
| Dentalcrete powder | 70 | 63 | 67.4 | 69 | 75 | 82 | 82 | 73 | 69 |
| Citric acid | 6 | | | | | | | | |
| Phosphorylcholine compound | | 7 | | | | | | | |
| Potassium poly vinyl sulfate | | | 7.5 | | | | | | |
| Sodium polyacrylate | | | | 8 | | | | | 2 |
| Polyacrylic acid | | | | | 25 | | | | |
| Dilute polyacrylic acid | | | | | | 18 | | | |
| Methacrylic acid (25%) | | | | | | | 18 | | |
| Polystyrene sulfonate sodium salt | | | | | | | | 4 | 2 |

These compositions accelerated the setting of the powders compared to compositions containing just water, but did not have the washout-resistance that the liquids in Example F conferred.

Example K

In this Example K, the endodontic biocompatibility of a material made according to the present invention (composition No. 1 in Example H mixed with liquid carrier No. 4 in Example F in a powder to liquid ratio of 4:1) and commercially-available White ProRoot MTA Sealer/water were tested. Four dogs were the subjects of this protocol for root canal treatment. The four maxillary anterior teeth, the maxillary $2^{nd}$ and $3^{rd}$ premolars, and the mandibular $2^{nd}$ $3^{rd}$, and $4^{th}$ premolars were used in the experimental design. Pre-operative and post-operative radiographs of the maxillary anterior teeth and the mandibular premolars were taken using the XCP radiographic system or with Occlusal intra-oral film. Pulpotomies were performed in the maxillary $2^{nd}$ and $3^{rd}$ premolars. Experimental or control materials were placed directly onto the coronal pulp

TABLE 10A

Pulpotomies Using Experimental Material/Average Scores

| | Inflammation | Pulp tissue organization | Reactional dentin formation | Dentinogenesis |
|---|---|---|---|---|
| Experimental | 0.7 | 1.2 | 2.7 | 1.3 |

In the histological sections evaluated, the vast majority of the samples exhibited no inflammation (average score less than 1—a score of zero indicates normal healthy tissue that one would find with no treatment.) The quality of the bone regenerated adjacent to the surgical site and the root tips was also normal in the majority of samples examined. There was significant layering of new bone that had invaginated into the surgical sites, surrounded by new osteoblasts on it surface. Layering of the new inorganic matrix (future bone forming cells) was evident. Few osteoclasts were seen, and no resorption of the material. Cementum deposition was seen on the majority of the resected dentinal surfaces. The average score was 1.8 for ERTM1, indicating that close to 50% of the root apertures were covered with varying layers of cementum covering the root aperture, of various thicknesses and morphological characteristics. Apical periodontal ligament formation was normal in all cases. Functionally oriented collagen fibers surrounded the root ends in many sections. The majority of samples had these fibers inserted into the new cementum or bone that had formed during healing. The presence of root surface resorption was very limited (score=0.2 for experimental material). Where found, the resorption itself was not adjacent to the experimental material. Some cellular destruction at the furcations was seen, due to furcation exposure to the destructive oral environment. However, when protected from exposure, good healing was observed. Some furcal perforation sites were lost during decoronation of the samples, where the furca can be very high in canine anatomy.

In the grading of the pulpotomy specimens the majority of cases exhibited minimal to no inflammation. A wide range of pulpal morphologies were seen, ranging from normal tissue to some disorganization of the odontoblastic layer, to total disorganization of the pulpal tissue morphology. However, even in cases in which there was total disorganization of the pulpal tissue, evidence was seen of moderate formation of hard tissue deposition beneath the experimental material. This hard tissue indicates that the pulpal disorganization may have been an artifact during specimen preparation. Few cases exhibited highly organized dentinogenesis at 60 days; however, the hard tissue barriers that did form were dense and thick with some evidence of normal dentinogenesis at the lateral borders (tubular dentin formation).

The experimental material did contribute to repair of periradicular tissues, including the periodontium. A dentinal barrier was formed that protected the pulps in the traumatizing pulpotomy. No resorption of the material was seen.

In summary, the experimental material was biocompatible with the periapical and pulpal tissues of these canine subjects after 60 days. The material was suitable for use in contact with these tissues to induce healing and repair of tissues. All of the specific indications tested were satisfactory both radiographically and histologically.

Handling

The composition of this invention has optimum handling. The calcium silicates and aluminates, handle better when coarse particles are eliminated, and the water soluble substances noted herein are combined. The handling improvements make it significantly easier for a clinician to use these hydraulic materials for dental procedures, placing them at the point of disease or trauma.

Working and Setting Times

The composition of this invention has optimum working and setting times. Working time is measured according to Dental Standards ISO9917 or ISO 6876 (water-based dental cements) and is the period of time measured from the initial mixing of the ingredients to the point when the material begins to harden—the material can be manipulated during this time with no adverse effect on the properties of the material. The net setting time is also measured according to Dental Standards ISO-9917 and is the period of time measured from the end of mixing of the ingredients to the point when the material sets. More particularly, the net setting time is measured by casting the material in a mold. After the mixing has been completed, the indenter device is vertically lowered onto the surface of the cement and it is allowed to remain there for 5 seconds. A trial run is carried out to determine the approximate setting time, repeating the indentations at 30 second intervals until the needle fails to make a complete circular indentation in the cement, when viewed using 2× magnification. The needle is cleaned, if necessary, between indentations. The process is repeated, starting the indentation at 30 seconds before the approximate setting time thus determined, making indentations at 10 second intervals. The net setting time is recorded as the time elapsed between the end of mixing and the time when the needle fails to make a complete circular indentation in the cement. A similar testing procedure, ISO 6876 (root canal sealers) can be used for measuring the working and setting times of the composition.

In general, the compositions of this invention have a working time in the range of about five (5) minutes to about sixty (60) minutes. The exact working time period of the composition depends on its specific formulation. As discussed above, different formulations can be used for root canal apicoectomies, apexification, perforation repair, obturation, pulpotomies, pulp-capping, cavity liners, root-end resorption repair, and root canal sealing. The final setting time is generally within the range of about ninety (90) minutes to about twelve (12) hours. This shortened working time allows the dental practitioner to handle and place the material more effectively. The clinician can fill or repair the root canal and see the material begin to harden and form a rock-like substance. The clinician is better able to work and shape the material. After the clinician applies the material to the targeted area, it remains in place. The material has good consistency and does not migrate away from the area. This allows a clinician to clean-up a site by rinsing when a surgical or vital pulp therapy procedure is performed and blood is present.

Furthermore, additional dental material, such as a restorative composite, can be placed over the root canal filling/sealing material as it begins to set. Used for pulp-capping or cavity liner procedures, the placed root canal filling/sealing material bonds to the root dentin and, preferably, to any other materials (for example, gutta-percha or dental composite) being used to fill the root canal or treat the vital pulp. As the root canal filling/sealing composition sets and hardens, it provides a solid barrier to bacterial and fluid leakage in the root canal system. The fluid pathways between the root canal system and surrounding tissue are tightly sealed off. Furthermore, the root canal filling/sealing material is bactericidal.

Workers skilled in the art will appreciate that various modifications can be made to the illustrated embodiments and description herein without departing from the spirit and scope of the present invention. It is intended that all such modifications within the spirit and scope of the present invention be covered by the appended claims.

What is claimed is:

1. A composition for treating a root canal in a tooth, comprising:
   a) about 1 to about 80% by weight of particulate material including:
      (i) calcium silicate, calcium aluminate, tetracalcium aluminoferrite, calcium phosphate, calcium sulfate, silica, alumina, calcium oxide, calcium hydroxide or mixtures thereof; and
      (ii) hydroxyapatite;
   (b) about 1 to about 50% by weight liquid carrier comprising:
      (i) water-soluble polymer,
      (ii) surfactant, the surfactant is selected from the group consisting of alkyl sulfates, alkyl ether sulfates, and sarcosinates, and mixtures thereof; and
      (iii) water,
      wherein the ratio of the surfactant to water-soluble polymer being no greater than 6 to 1, and
   wherein the particulate and liquid carrier being mixed together to form a hydrate gel material that can harden.

2. The composition of claim 1, wherein the water-soluble polymer is selected from the group consisting of polyvinyl alcohols, polyvinyl-pyrrolidone (PVP), partially hydrolyzed polyvinyl acetates, (PVAc), polyacrylic acid (PAA), and polymethacrylic acid (PMA), and copolymers and mixtures thereof.

3. The composition of claim 1, further comprising about 1 to about 60% by weight of a radiopaque component.

4. The composition of claim 3, wherein the radiopaque component is selected from the group consisting of bismuth oxide, barium sulfate, tantalum oxide, cerium oxide, tin oxide, zirconium oxide compounds and radiopaque glasses containing tantalum, barium and strontium, and mixtures thereof.

5. The composition of claim 1, wherein the particulate material comprises a mixture of tricalcium silicate and dicalcium silicate particles.

6. The composition of claim 1, wherein the particulate material comprises about 20 to about 80 wt. % tricalcium silicate; about 20 to about 50 wt. % dicalcium silicate; about 1 to about 20 wt. % tricalcium aluminate, about 1 to about 8 wt. % tetracalcium aluminoferrite; about 1 to about 15 wt. % calcium sulfate dihydrate, and about 1 to about 50 wt. % radiopaque component.

7. The composition of claim 6, wherein the particulate has an average particle size in the range of about 1 µm to about 40 µm.

8. The composition of claim 6, wherein the particulate material has an average particle size in the range of about 1 µm to about 15 µm.

9. The composition of claim 1, wherein the composition further comprises a humectant.

10. The composition of claim 1, further comprising about 1 to about 40% by weight of a radiopaque component.

11. The composition of claim 2, wherein
   the particulate material further comprises about 1 to about 60% by weight of a radiopaque component, the radiopaque component being selected from the group consisting of bismuth oxide, barium sulfate, tantalum oxide, cerium oxide, tin oxide, zirconium oxide compounds and radiopaque glasses containing tantalum, barium and strontium, and mixtures thereof.

12. The composition of claim 11, wherein the particulate material comprises about 20 to about 80 wt. % tricalcium silicate; about 20 to about 50 wt. % dicalcium silicate; about 1 to about 20 wt. % tricalcium aluminate, about 1 to about 8 wt. % tetracalcium aluminoferrite; about 1 to about 15 wt. % calcium sulfate dihydrate, and about 1 to about 50 wt. % radiopaque component.

13. The composition of claim 12, wherein the particulate material has an average particle size in the range of about 1 µm to about 15 µm.

14. The composition of claim 12, wherein the water-soluble polymer is present in an amount from about 5% to about 80% by weight of the liquid carrier.

15. The composition of claim 14, wherein the surfactant is present in an amount from about 1% to about 80% by weight of the liquid carrier.

16. The composition of claim 15, wherein the water is present in an amount from about 1% to about 95% by weight of the liquid carrier.

17. A composition for treating a root canal in a tooth, comprising:
   a) about 1 to about 80% by weight of particulate material including
      (i) about 20 to about 80 wt. % tricalcium silicate;
      (ii) about 20 to about 50 wt. % dicalcium silicate;
      (iii) about 1 to about 20 wt. % tricalcium aluminate,
      (iv) about 1 to about 8 wt. % tetracalcium aluminoferrite;
      (v) about 1 to about 15 wt. % calcium sulfate dihydrate, and
      (vi) about 1 to about 50 wt. % radiopaque component; and
   about 1 to about 50% by weight liquid carrier including
      (i) a water-soluble polymer being present in an amount from about 5% to about 80% by weight of the liquid carrier, the water-soluble polymer is selected from the group consisting of polyvinyl alcohols, polyvinyl-pyrrolidone (PVP), partially hydrolyzed polyvinyl acetates, (PVAc), polyacrylic acid (PAA), and polymethacrylic acid (PMA), and copolymers and mixtures thereof;
      (ii) a surfactant being present in an amount from about 1% to about 80% by weight of the liquid carrier, the surfactant is selected from the group consisting of alkyl sulfates, alkyl ether sulfates, and sarcosinates, and mixtures thereof; and
      (iii) water being present in an amount from about 1% to about 95% by weight of the liquid carrier;
   wherein the particulate and liquid carrier being mixed together to form a hydrate gel material that can harden
   wherein the ratio of the surfactant to water-soluble polymer being no greater than 6 to 1.

18. The composition of claim 17, wherein the ratio of the surfactant to water-soluble polymer being no greater than 3 to 1.

19. The composition of claim 17, wherein the particulate material further comprises about 1 to about 30% by weight of hydroxyapatite.

20. The composition of claim 19, wherein the radiopaque component is selected from the group consisting of bismuth oxide, barium sulfate, tantalum oxide, cerium oxide, tin oxide, zirconium oxide compounds and radiopaque glasses containing tantalum, barium and strontium, and mixtures thereof.

21. The composition of claim 20, wherein the particulate material has an average particle size in the range of about 1 µm to about 15 µm.

* * * * *